(12) United States Patent
Minami et al.

(10) Patent No.: US 9,204,831 B2
(45) Date of Patent: Dec. 8, 2015

(54) BRAIN STATE SUPPORT APPARATUS AND PROGRAM

(76) Inventors: Mitsunori Minami, Fukui-ken (JP); Toshinori Kato, Tokyo (JP)

( * ) Notice: Subject to any disclaimer, the term of this patent is extended or adjusted under 35 U.S.C. 154(b) by 165 days.

(21) Appl. No.: 13/332,832

(22) Filed: Dec. 21, 2011

(65) Prior Publication Data

US 2013/0165739 A1 Jun. 27, 2013

(51) Int. Cl.
| | | |
|---|---|---|
| *A61M 21/00* | (2006.01) | |
| *A61B 5/1455* | (2006.01) | |
| *A61N 1/36* | (2006.01) | |
| *A61B 5/00* | (2006.01) | |
| *A61B 5/16* | (2006.01) | |

(52) U.S. Cl.
CPC ........ *A61B 5/14553* (2013.01); *A61N 1/36025* (2013.01); *A61B 5/0075* (2013.01); *A61B 5/165* (2013.01)

(58) Field of Classification Search
CPC . A61N 1/36025; A61N 1/36; A61N 1/36014; A61N 1/36017; A61N 5/0619; A61B 5/14553; A61B 5/145; A61B 5/14535; A61B 5/1455; A61B 5/0075; A61B 5/165; A61H 39/00; A61H 39/002; A61M 37/00; A61M 37/0015
USPC .................. 600/26–28, 320, 328; 607/2, 45; 128/897–899
See application file for complete search history.

(56) References Cited

U.S. PATENT DOCUMENTS

| | | | | |
|---|---|---|---|---|
| 5,135,468 | A * | 8/1992 | Meissner ........................ | 600/28 |
| 6,986,747 | B2 * | 1/2006 | McCulloch et al. .......... | 600/558 |
| 2007/0142874 | A1 * | 6/2007 | John .............................. | 607/45 |
| 2007/0239039 | A1 * | 10/2007 | Yang et al. .................... | 600/483 |
| 2008/0269832 | A1 * | 10/2008 | Wong et al. .................... | 607/42 |
| 2009/0171164 | A1 * | 7/2009 | Jung et al. .................... | 600/300 |

FOREIGN PATENT DOCUMENTS

JP 2002-177282 6/2002

OTHER PUBLICATIONS

"Comparison of Electroacupuncture Frequency-related Effects on Heart Rate Variability in Healthy Volunteers: A Randomized Clinical Trial" by J-H Lee, K-H Kim, J-W Hong, W-C Lee, and S Koo, J Acupunct Meridian Stud 2011; 4(2):107-115.*
"Near-infrared spectroscopy for objectifying cerebral effects of needle and laserneedle acupuncture" by G. Litscher and D. Schikora, Spectroscopy 16 (2002) 335-342.*

* cited by examiner

*Primary Examiner* — Jacqueline Cheng
*Assistant Examiner* — Sunita Reddy
(74) *Attorney, Agent, or Firm* — Westerman, Hattori, Daniels & Adrian, LLP

(57) ABSTRACT

The brain state support apparatus 1 comprises a stimulus applying device 2, a light detecting device 3, a calculating section 13 for calculating the changed amount of total hemoglobin and the changed amount of oxygen saturation based on the light information, a determination section 14 for determining whether the brain state of the human body is in at least one of a relaxation mode, a concentration mode and an intermediate mode, based on the changed amount of total hemoglobin and the changed amount of oxygen saturation by applying a stimulus of an electrical signal having a predetermined frequency to the acupoint of the human body through the stimulus applying device 2; and a stimulus adjusting section 15 for adjusting a quantity of stimulus to be applied to an acupoint of the human body by the stimulus applying device 2.

6 Claims, 13 Drawing Sheets

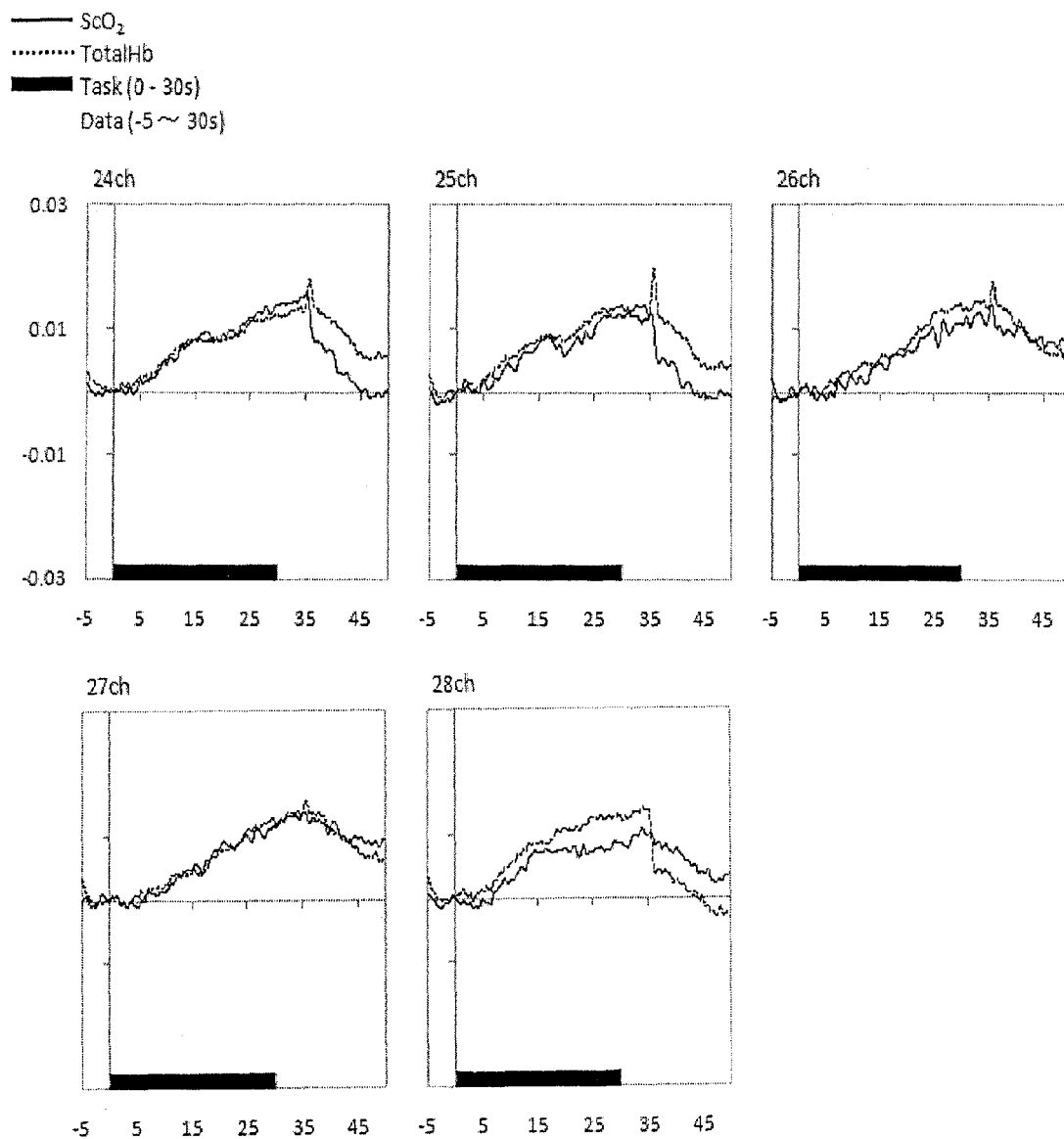

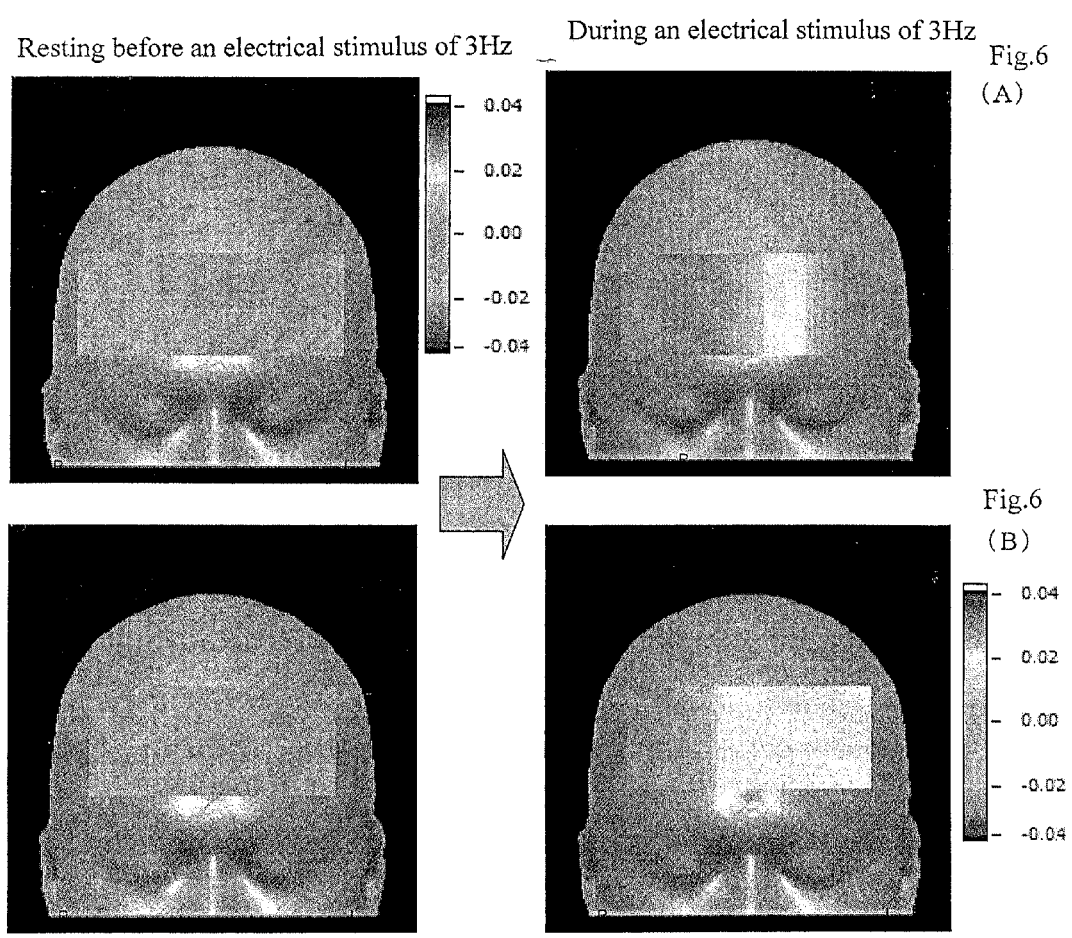

BRAIN STATE SUPPORT APPARATUS AND PROGRAM

TECHNICAL FIELD

The present invention relates to a brain state support apparatus and program for supporting the brain state of the human body and particularly to a brain state support apparatus and program for supporting the brain state such that it can be maintained at a relaxation mode and an intensive mode or shifted to the other states using the near-infrared spectroscopy (NIRS).

BACKGROUND ART

In the past, various means such as massage, acupuncture and sleeping have been adopted to relax the brain state or to increase the power of concentration. (This technique will be referred to "the prior art 1" later.)

Patent document 1 discloses a method of measuring changed concentrations in oxyhemoglobin and deoxyhemoglobin using the near-infrared spectroscopy before an external stimulus to be evaluated is applied to a test subject and after it has been applied to the same test subject, then hearing the subjective amenity from the test subject when said external stimulus is applied thereto, and estimating the appropriateness of the external stimulus to the human body based on the measurements and the subjective amenity.

The near-infrared spectroscopy means a method of irradiating a brain with a feeble near-infrared light (e.g., 680-1300 nanometers) through the skull and scalp of a human body and measuring the changed concentrations of oxyhemoglobin (Oxy-H b; $HbO_2$) and deoxyhemoglobin (Deoxy-Hb; Hb) in the blood in the brain surface immediately inside the brain (cerebral cortex). (This method will be referred to "the prior art 2" later.)

Patent Document 1

Japanese Laid-Open Patent Application 2002-177282

SUMMARY OF THE INVENTION

Problems to be Solved by the Invention

The prior art 1 raises a problem in that it cannot be objectively known how brain state is actually influenced by massage, acupuncture, sleep.

Further, the prior art 1 raises another problem in that after having received massage and acupuncture, the effectiveness will be disappeared without continuation as soon as the brain is tensed or directed to another thing.

With the acupuncture, a beginner might have a resistance for damaging a body.

On the other hand, the prior art 2 can objectively know what kind of state the brain state is actually in. However, the prior art 2 raises a problem in that the brain state cannot be maintained at the same state or supported to shift the brain state from one to another.

Further, it is difficult that the prior art 2 judges the brain state precisely since it does not use an oxygen saturation (exchange) index to determine the cerebral oxygen consumption.

The present invention is made to solve the above problems, its object being to provide a brain state support apparatus and program which can objectively know what kind of state a brain state is in and which can support the brain state for being maintained at the same state and for shifting the brain state from one to another.

Means to Solve the Problems

The present invention provides a brain state support apparatus being characterized in that it comprises:
stimulus applying means for stimulating an acupoint in the human body with an electrical signal of a predetermined frequency;
light detection means comprising a light emitting section for irradiating the human body with a light at a predetermined region, and a light receiving section for receiving and sensing a light emitted from the interior of the human body; and
a main apparatus body for controlling the stimulus applying means and the light detection means,
said main apparatus body comprising:
calculating means for calculating the changed amount of total hemoglobin that is the sum of the changed amount of oxyhemoglobin plus the changed amount of deoxyhemoglobin and the changed amount of oxygen saturation that is a difference between the changed amount of the oxyhemoglobin and the changed amount of the deoxyhemoglobin, based on light information detected by the light detecting means;
determination means for determining whether the brain state of the human body is in at least one of a relaxation mode, a concentration mode and an intermediate mode, based on the changed amount of total hemoglobin and the changed amount of oxygen saturation change which are calculated by the calculating means by applying a stimulus of an electrical signal having a predetermined frequency to the acupoint of the human body; and
stimulus adjusting means for adjusting the quantity of stimulus which is applied to the acupoint of the human body with the electrical signal having a predetermined frequency by the stimulus applying means such that the mode of the brain state determined by the determination means can be maintained or shifted to the other mode of the brain state.

For example, the acupoint of the human body stimulated by the stimulus applying means is in the region of left thumb.

For example, the region detected by the light detecting means is the cerebral frontal lobe.

The determination means may be configured to determine that the brain state is in the relaxation mode when the changed amount of total hemoglobin is increased and also the changed amount of oxygen saturation is increased by stimulating the acupoint of the human body with an electrical signal of a first frequency; to determine that the brain state is in the concentration mode when the changed amount of total hemoglobin is decreased and also the changed amount of oxygen saturation is decreased by stimulating the acupoint of the human body with an electrical signal of a second frequency; and to determine that the brain state is in the intermediate mode in the other cases.

The stimulus adjusting means may be configured to stimulate the acupoint of the human body with the electrical signal of the first frequency at a predetermined interval of time when it is wanted to maintain the brain state at the relaxation mode or to shift it to the relaxation mode; and to stimulate the acupoint of the human body with the electrical signal of the second frequency at a predetermined interval of time when it is wanted to maintain the brain state at the concentration mode or to shift it to the concentration mode.

For example, the first frequency is 3 Hz and the second frequency is 10 Hz.

The stimulus adjusting means may be configured to increase the quantity of stimulus when the brain state is to be shifted to the other modes rather than when the brain state is to be maintained at the same mode.

The present invention also provides a program characterized by causing a process to perform in the main apparatus body of the brain state support apparatus.

Advantages of the Invention

According to the present invention, the following advantages are provided:

(1) The desired brain state can be provided simply and easily without massage, acupuncture or sleep.

(2) The brain state can be objectively known.

Additionally, the brain state can be maintained in the same state and can be shift to the other states. When a person is tired, has many idle thoughts or is irritated with many idle thoughts or not placed in concentration, for example, the present invention can place the brain state in the concentration mode to increase the power of concentration.

When a person have a work and if the present invention determines that the person is in the relaxation mode, the present invention can forcibly shift his or her brain state to the concentration mode.

On the contrary, the present invention can shift the brain state from the concentration mode to the relaxation mode.

According to the present invention, still further, an intensified concentration state or a relaxation state can be prolonged.

BRIEF DESCRIPTION OF THE DRAWINGS

FIG. 2 (B) illustrates the stimulus applying device attached to a thumb;

FIG. 2 (C) is a front view illustrating a stimulus applying device according to another embodiment of the present invention; and FIG. 2 (D) illustrates the stimulus applying device of FIG. 2 (C) attached to a thumb.

FIG. 5 shows graphs showing changes in the changed amount of total hemoglobin and the changed amount of oxygen saturation in the frontal lobe when an electrical stimulus of 3 Hz is applied to a region adjacent to the center of the side of the hand palm between the first and second joints of the left hand thumb.

FIG. 6 (A) visually illustrates a change in the changed amount of total hemoglobin in the frontal lobe on resting before an electrical stimulus of 3 Hz is applied to a region adjacent to the center of the side of the hand palm between the first and second joints of the left hand thumb and on stimulation after such an electrical stimulus has been applied to the same region.

FIG. 6 (B) visually illustrates a change in the changed amount of oxygen saturation.

FIG. 8 (B) visually illustrates a change in the changed amount of oxygen saturation.

FIG. 10 (B) visually illustrates a change in the changed amount of oxygen saturation.

FIG. 12 (B) visually illustrates a change in the changed amount of oxygen saturation.

BEST MODE FOR CARRYING OUT THE INVENTION

One embodiment of the present invention will now be described with reference to the drawings.

Figure 1:
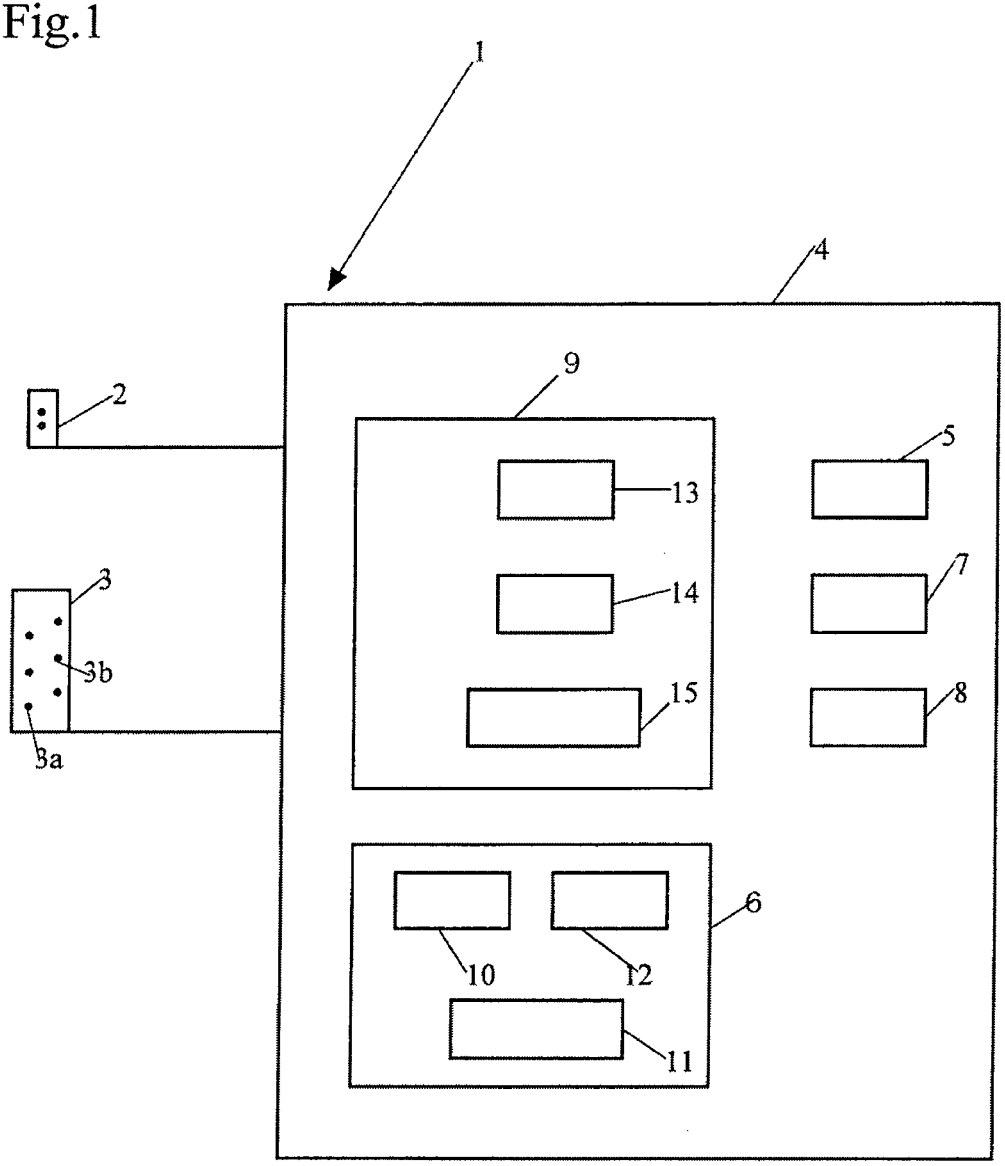
FIG. 1 is a block diagram illustrating the structure of a brain state support apparatus according to one embodiment of the present invention.

FIG. 1 is a block diagram showing the arrangement of a brain state support apparatus 1 according to one embodiment of the present invention.

As can be seen from FIG. 1, the brain state support apparatus 1 according to the present invention comprises a stimulus applying device 2 mounted on the human body at its acupoint (e.g., a part of the left hand thumb) and configured to stimulates the part with an electrical signal having a predetermined frequency, and a light detecting device 3 comprising a light emitting section (light-emitting element) 3a mounted on a predetermined region of the human body (e.g., the cerebral frontal lobe) and configured to irradiate this region with light and a light receiving section (light-receiving element) 3b configured to receive and sensing light emitted from the interior of the human body, and a main apparatus body 4.

Figure 2:
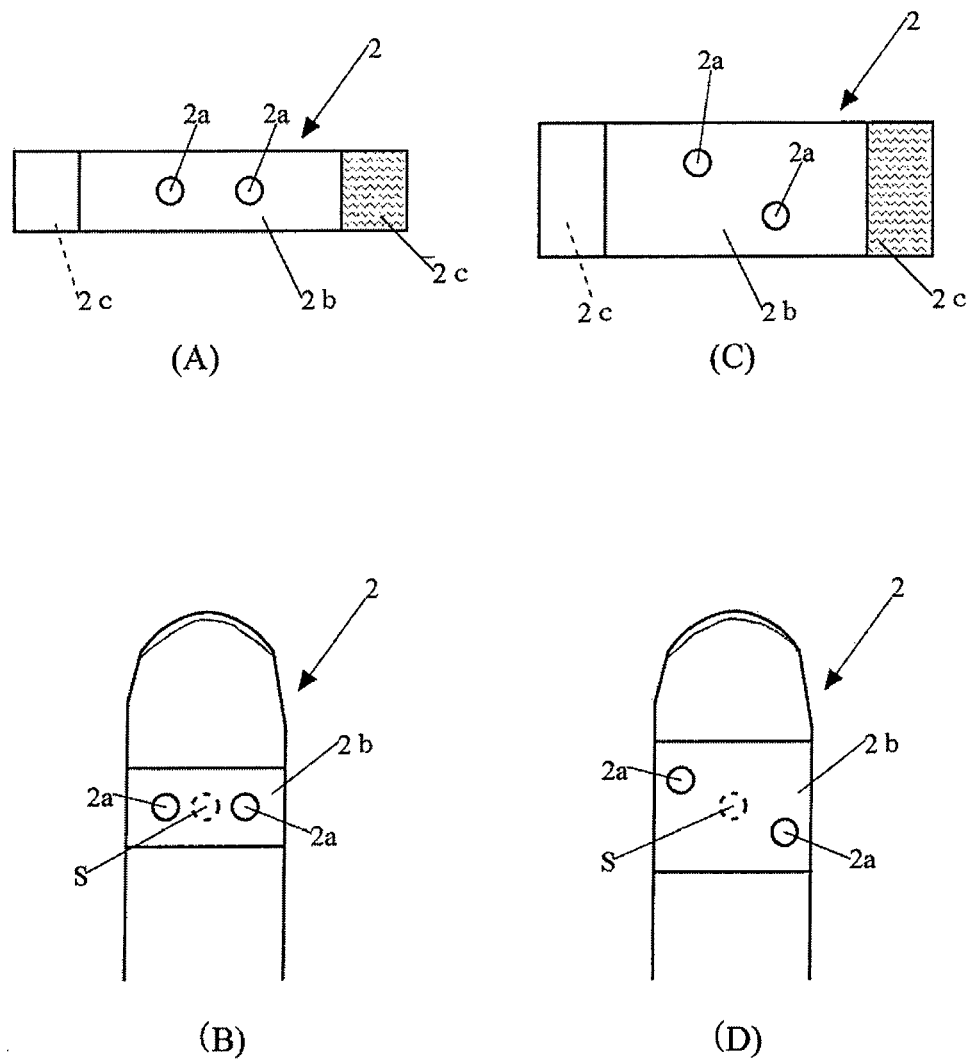
FIG. 2 (A) is a front view showing a stimulus applying device.

FIG. 2 (A) is a front view showing a stimulus applying device 2; FIG. 2 (B) illustrates the stimulus applying device 2 attached to a thumb; FIG. 2 (C) is a front view illustrating a stimulus applying device 2 according to another embodiment of the present invention; and FIG. 2 (D) illustrates the stimulus applying device 2 of FIG. 2 (C) attached to a finger other than the thumb.

As shown in FIGS. 2 (A and B), the stimulus applying device 2 comprises a pair of stimulating portions 2a mounted on the human body in engagement with its regions to be stimulated for stimulating the regions with electrical signals of a predetermined frequency, and a band portion 2b releasably mounted on a finger for holding the stimulating portions 2a.

The pair of stimulating portions 2a may be mounted, for example, on a finger and spaced from each other with a distance between about 3 and 10 mm.

As shown in FIG. 2 (B), the pair of stimulating portions 2 are mounted on the opposite sides of a region S to be stimulated. The distance between the stimulating portions 2a may be suitably selected depending on a desired acupoint of the human body.

The band portion 2b may include loop fasteners 2c (e.g., magic tapes (registered trademark)) attached thereto on the opposite ends thereof.

The stimulus applying device 2 can be fixedly mounted on a finger by winding the band portion 2b around finger and engaging the loop fastener 2c with each other.

As shown in FIGS. 2 (C) and (D), however, the width of the band portion 2b may be increased such that the pair of stimulating portions 2a may be located spaced away from each other in the diagonal direction.

The light detecting device 3 may have a harness which can be mounted on the human body at a predetermined region.

The light emitting and receiving sections 3a, 3b may be mounted on the harness and spaced apart from one another with a predetermined spacing.

The main apparatus body 4 is configured to control the operations of the stimulus applying device 2 and light detecting device 3 and to perform the input/output, computation and storage of various data.

The main apparatus body 4 comprises an input section 5, an output section 6, a communication section 7 and a storage section 8 and a control section 9.

The input section 5 is used to input various data and may be in the form of a keyboard, a numeric keypad, a mouse, a mark sheet reader or an optical character recognition (OCR) unit.

The output section 6 is used to output various data and comprises a display section 10 such as a monitor or display for displaying various data, a speaker 11 for outputting voice data and a print section 12 for printing various data.

The communication section 7 is connected to a communication network such as Internet (Data Transfer Network using Transmission Control Protocol/Internet Protocol (TCP/IP)) or Local Area Network (LAN) for transmitting and receiving various data.

For example, the communication section 7 may be in the form of a modem, a terminal adaptor, a router or Digital Service Unit (DSU).

The storage section 8 is used to store various data and comprises a database.

The control section 9 comprises a calculating section 13 for calculating the changed amount of total hemoglobin that is the sum of the changed amount of oxyhemoglobin plus the changed amount of deoxyhemoglobin and the changed amount of oxygen saturation that is a difference between the changed amount of the oxyhemoglobin and the changed amount of the deoxyhemoglobin, based on light information detected by the light detecting device 3; a determination section 14 for determining whether the brain state of the human body is in at least one of a relaxation mode, a concentration mode and an intermediate mode, based on the changed amount of total hemoglobin and the changed amount of oxygen saturation change which are calculated by the calculating section 13 by applying a stimulus of an electrical signal having a predetermined frequency to the acupoint of the human body through the stimulus applying device 2; and a stimulus adjusting section 15 for adjusting the quantity of stimulus which is applied to the acupoint of the human body with the electrical signal having a predetermined frequency by the stimulus applying means such that the mode of the brain state determined by the determination means can be maintained or shifted to the other mode of the brain state.

The determining section 14 is configured to determine that the brain state is in the relaxation mode when the changed amount of total hemoglobin is increased and also the changed amount of oxygen saturation is increased by stimulating the acupoint of the human body with an electrical signal of a first frequency (e.g., 3 Hz); to determine that the brain state is in the concentration mode when the changed amount of total hemoglobin and the changed amount of oxygen saturation are decreased by stimulating the acupoint of the human body with an electrical signal of a second frequency (e.g., 10 Hz); and to determine that the brain state is in the intermediate mode in the other cases.

The stimulus adjusting section 15 is configured to stimulate the acupoint of the human body with the electrical signal of the first frequency (e.g., 3 Hz) at a predetermined interval of time when it is wanted to maintain the brain state at the relaxation mode or to shift it to the relaxation mode; and to stimulate the acupoint of the human body with the electrical signal of the second frequency (e.g., 10 Hz) at a predetermined interval of time when it is wanted to maintain the brain state at the concentration mode or to shift it to the concentration mode.

The stimulus adjusting section 15 is operative to increase the quantity of stimulus when it is wanted to shift the brain state to the other mode rather than when it is wanted to maintain the brain state at the same mode.

In this regard, the frequency of the electrical signal for stimulation is not limited to the above numerical level.

Figure 3:
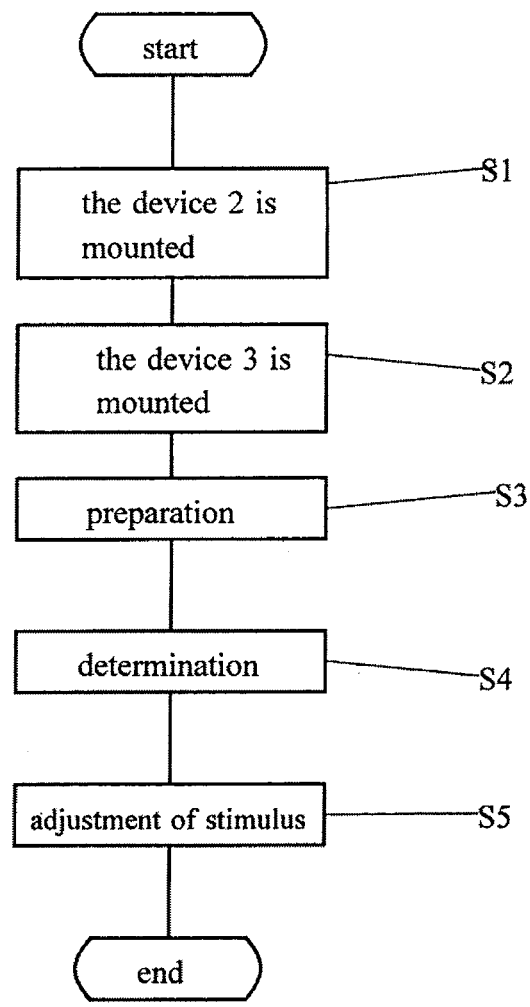
FIG. 3 is a flowchart illustrating the operation of a brain state support apparatus according to one embodiment of the present invention.

FIG. 3 is a flowchart illustrating the operation of a brain state support apparatus 1 according to one embodiment of the present invention.

First of all, the stimulus applying device 2 is mounted on the human body at a region adjacent to its desired acupoint (e.g., an acupoint on the left hand thumb) (Step S1).

Subsequently, the light detecting device 3 is mounted on the human body at a predetermined region (e.g., cerebral frontal lobe) (Step S2).

Subsequently, the apparatus is prepared for determination of the brain state (Step S3).

In this Step S3, a stimulus of 3 Hz is applied to the left hand thumb for 5-10 seconds to determine the minimum strength of stimulus that is slightly felt by the skin thereof.

Further, the same stimulus of 3 Hz is applied to the left hand thumb for 5-10 seconds to determine the maximum strength of stimulus by which the skin thereof feels an ache.

Next, the intermediate (50%) strength of the 3 Hz stimulus is calculated using the following formula:

the intermediate (50%) strength of the 3 Hz stimulus= (the minimum strength of stimulus+the maximum strength of stimulus)/2

Further, a stimulus of 10 Hz is applied to the left hand thumb for 5-10 seconds to determine the minimum strength of stimulus that is slightly felt by the skin thereof.

Further, the same stimulus of 10 Hz is applied to the left hand thumb for 5-10 seconds to determine the maximum strength of stimulus by which the skin thereof feels an ache.

Next, the intermediate (50%) strength of the 10 Hz stimulus is calculated using the following formula:

the intermediate (50%) strength of the 10 Hz stimulus=(the minimum strength of stimulus+the maximum strength of stimulus)/2

The maximal strength of stimulus is set by setting the voltage and current of the electrical stimulation.

Subsequently, the brain state is determined by the determining section 14 (Step S4).

Here, the brain reaction to be provided by the stimulus of 3 Hz to the left hand thumb is defined as a relaxation mode (R mode).

This mode indicates a state in which the brain is relaxed.

Further, the brain reaction to be provided by the stimulus of 10 Hz is defined as a concentration mode (B mode).

This mode indicates a state in which the brain acts to increase the concentration and intelligence. Such a state is suitable for a study, for example.

In this Step S4, the intermediate strength of stimulus of 3 Hz determined in Step S2 is applied to the region of the left hand thumb in a pattern of 30 second stimulation—30 second rest—30 second stimulation—30 second rest.

If there is no reaction after the stimulation has been continued for 30 seconds, it is determined that the brain state is already in a stronger R mode.

If there is a reaction of R mode, it is determined that the brain state is in a lower R mode or the B mode or the intermediate mode.

Further, the intermediate strength of stimulus of 10 Hz determined in Step S2 is applied to the region of the left hand thumb in a pattern of 30 second stimulation—30 second rest—30 second stimulation—30 second rest.

If there is no reaction after the stimulation for 30 seconds, it is determined that the brain state is already in a stronger B mode.

If there is a reaction of B mode, it is determined that the brain state is in a lower B mode or the R mode or the intermediate mode.

The results of determination are displayed on the display section 10 such as a monitor or a display with sounds being outputted through the speaker 11.

Further, the results of determination may be printed by the printing portion 12 or transmitted as data by the communication section 7 through the network.

Subsequently, the degree of stimulation is adjusted by the stimulus adjusting section 15 (Step S5).

In this Step S5:
1) When it is judged by the determining device 14 that the brain state is in the B mode, the stimulation is adjusted such that the brain state can be shifted to the R mode.
2) When it is judged by the determining device 14 that the brain state is in the R mode, the stimulation is adjusted such that the brain state can be maintained in the R mode.
3) When it is judged by the determining device 14 that the brain state is in the B mode, the stimulation is adjusted such that the brain state can be maintained in the B mode.
4) When it is judged by the determining device 14 that the brain state is in the R mode, the stimulation is adjusted such that the brain state can be shifted to the B mode.

Either of the above cases can be selected through the input section 5.

The adjustment of each case may be practiced as follows.

1) Shift from B to R
The stimulus of 50% of the 3 Hz stimulus determined in Step S3 is applied for 60 seconds and then halted for 30 seconds. Further, the stimulus of 75% is applied for 60 seconds and halted for 30 seconds.

If the brain state is not shifted to the R mode, the 100% stimulus is further applied for 60 seconds.

In such a manner, the shift to R mode will be forced by increasing the quantity of stimulus.

2) Maintenance of R mode
The stimulus of 25% of the 3 Hz stimulus determined in Step S3 is applied for 30 seconds and then halted for 30 seconds. Further, the stimulus of 25% is applied for 30 seconds and halted for 30 seconds and applied for 30 seconds.

In such a manner, the R mode will be maintained by intermittently applying the same stimulus.

3) Maintenance of B mode
The stimulus of 25% of the 10 Hz stimulus determined in Step S3 is applied for 30 seconds and then halted for 30 seconds.

Further, the stimulus of 25% is applied for 30 seconds, then halted for 30 seconds and applied for 30 seconds.

In such a manner, the B mode will be maintained by intermittently applying the same stimulus.

4) Shift from R to B
The stimulus of 50% of the 10 Hz stimulus determined in Step S3 is applied for 60 seconds and then halted for 30 seconds. Further, the stimulus of 75% is applied for 60 seconds and then halted for 30 seconds.

If the brain state is not shifted to the B mode, the 100% stimulus is further applied for 60 seconds.

The shift to B mode will be forced by increasing the quantity of stimulus in such a manner.

In this regard, the adjustment of stimulus is not limited and can be suitably performed.

Experiments performed by the inventor will be described to prove that the brain state support apparatus 1 according to the present invention is useful.

In these experiments, the detection and record of the Hb concentration of cerebrocortical were practiced by using a near-infrared spectroscopy measuring equipment (Shimazu Corporation: FOIRE3000).

The sampling of the hemoglobin was 70 ms.

The recorded hemoglobin was oxyhemoglobin (oxy-Hb), and deoxyhemoglobin (deoxy-Hb).

The changed of total hemoglobin (total-Hb: the sum of oxy-Hb and deoxy-Hb) and the changed of oxygen saturation ($ScO_2$) are calculated to provide an index of cerebral COE reaction by the following calculating formulas:

the changed amount of total hemoglobin (concentration) [Total hemoglobin]=[Oxyhemoglobin]+[Deoxyhemoglobin]    formula (1)

The changed amount of oxygen saturation (concentration) (a brain function index which was found by Kato, one of the inventors)

[$ScO_2$] (oxygen saturation or oxygen exchange)=[Oxyhemoglobin]−[Deoxyhernoglobin]    formula (2)

Here, [Oxyhemoglobin] is the changed amount of oxyhemoglobin (concentration). [Deoxyhernoglobin] is the changed amount of deoxyhemoglobin (concentration).

A particularly important function index is a decrease of $ScO_2$=oxygen consumption.

An oxygenated region with reduced concentration of oxygen is particularly important.

The changed amount of total hemoglobin represents variations in the number of red blood cells in a voxel of an optical measurement region which is sandwiched between irradiation and detection probes.

If the changed amount of total hemoglobin increases, it means the increased number of red blood cells.

If the changed amount of total hemoglobin decreases, it means the decreased number of red blood cells.

The changed amount of oxygen saturation (oxygen exchange) indicates the changed concentration of oxygen in the capillary.

If the changed amount of oxygen saturation increases, it means the increased amount of oxygen in the blood vessel.

If the changed amount of oxygen saturation decreases, it means the decreased amount of oxygen in the blood vessel.

The increased amount of oxygen in the blood vessel means the delivery of red blood cells rich in oxygen.

The decreased amount of oxygen in the blood vessel means that oxygen in the capillary has been consumed by the nerve cells.

The results of experiments are indicated using two kinds of waveform indication and mapping indication.

The waveform indication shows time series variations while the mapping indication is a plot of integrated values for a predetermined period of task time (stimulus time).

Figure 4A:
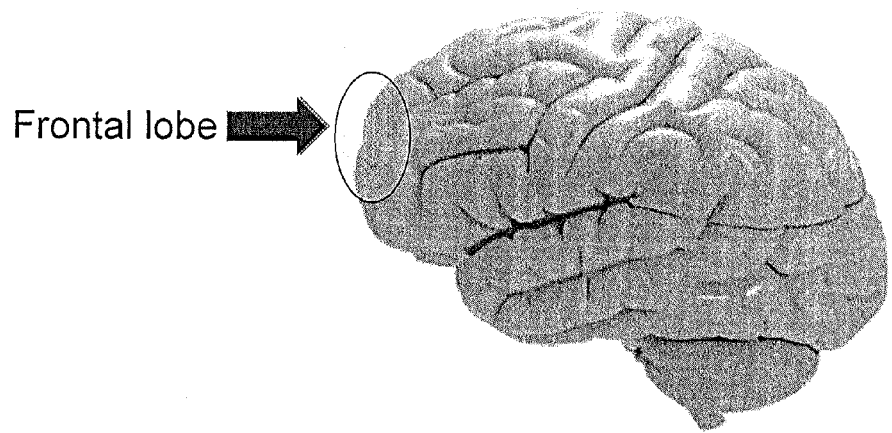
FIGS. 4 (A)-(C) illustrate a light detecting device.
Figure 4B:
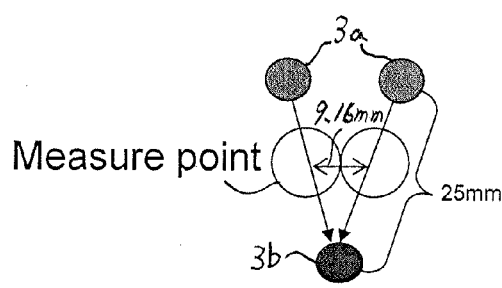
Figure 4C:
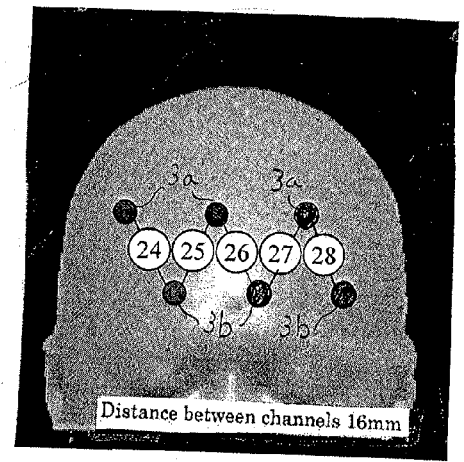

FIGS. 4 (A)-(C) illustrate the arrangement of the light detecting device 3.

The light detecting device 3 is disposed in an arrangement of high-density probe to cover the Brodmann's tenth area (frontal lobe) shown in FIG. 4 (A).

The light emitting portions 3a and light receiving portions 3b of the light detecting device 3 are disposed spaced apart from each other by such a distance as shown in FIG. 4 (B).

As can be seen from FIG. 4 (C), three light emitting portions 3a and three light receiving portions 3b are placed between the right and left brain regions.

Changes of the changed amount of total hemoglobin and changes of the changed amount of oxygen saturation are measured at five measurement points of 24 ch-28 ch in total.

FIG. 5 shows graphs showing changes in the changed amount of total hemoglobin and the changed amount of oxygen saturation in the frontal lobe when an electrical stimulus of 3 Hz is applied to a region adjacent to the center of the side of the hand palm between the first and second joints of the left hand thumb.

Here, the horizontal axis indicates time (s) while the vertical axis indicates the amount of change (mol/l). The time of stimulation is 30 seconds.

FIG. 6 (A) visually illustrates a change in the changed amount of total hemoglobin in the frontal lobe on resting before an electrical stimulus of 3 Hz is applied to a region adjacent to the center of the side of the hand palm between the first and second joints of the left hand thumb and on stimulation after such an electrical stimulus has been applied to the same region.

FIG. 6 (B) visually illustrates a change in the changed amount of oxygen saturation.

As can be seen from FIGS. 5 and 6, it was observed that dynamic increases of the changed amount of total hemoglobin and the changed amount of oxygen saturation over a widened range were derived by the electrical stimulation of 3 Hz. Particularly, these changes were conspicuously recognized in the frontal lobe.

Figure 7:
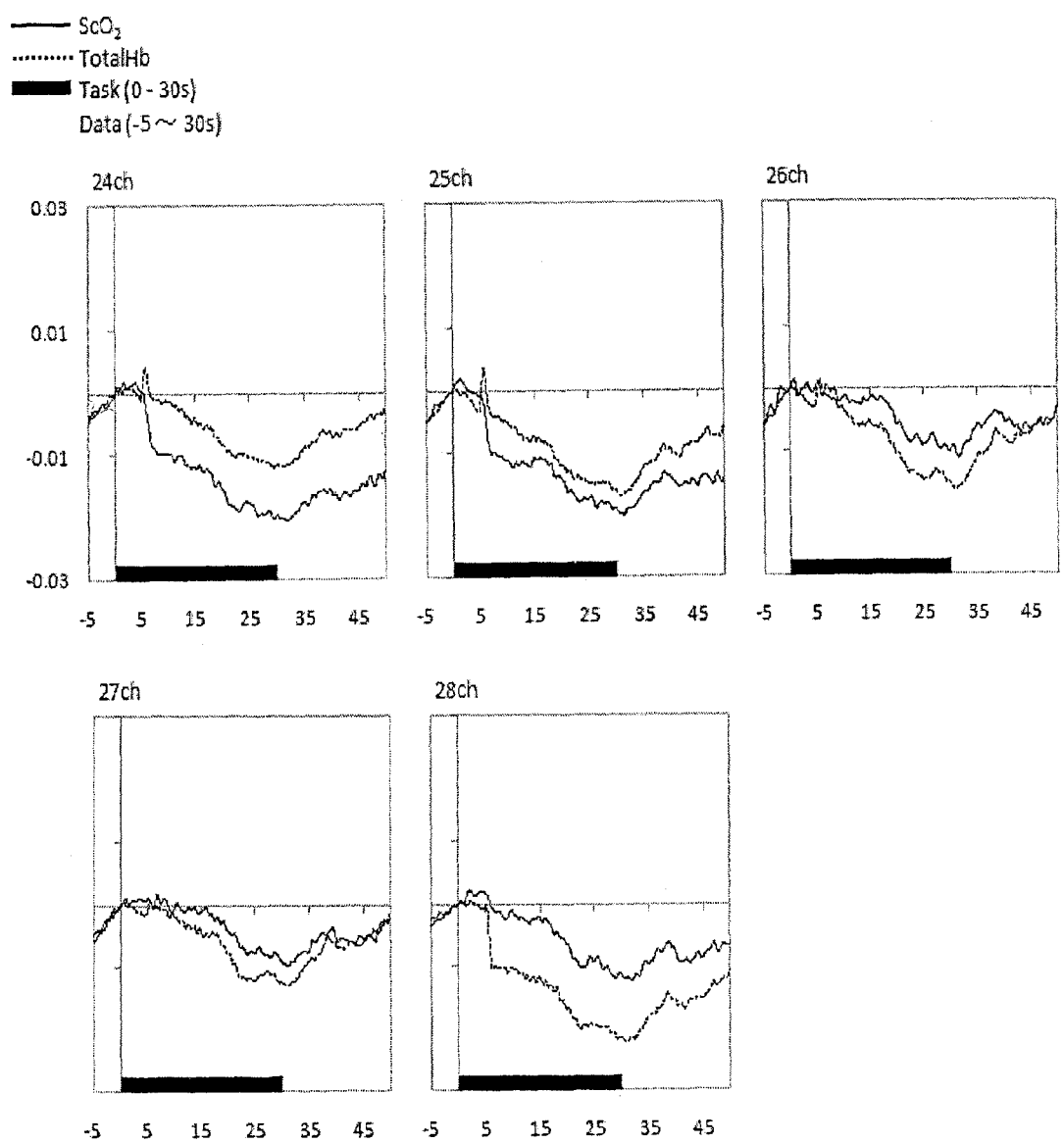
FIG. 7 shows graphs illustrating changes in the changed amount of total hemoglobin and the changed amount of oxygen saturation in the frontal lobe when an electrical stimulus of 10 Hz is applied to a region adjacent to the center of the side of the hand palm between the first and second joints of the left hand thumb.

FIG. 7 shows graphs showing changes in the changed amount of total hemoglobin and the changed amount of oxygen saturation in the frontal lobe when an electrical stimulus of 10 Hz is applied to a region adjacent to the center of the side of the hand palm between the first and second joints of the left hand thumb.

Here, the horizontal axis indicates time (s) while the vertical axis indicates the amount of change (mol/l). The time of stimulation is 30 seconds.

Figure 8:
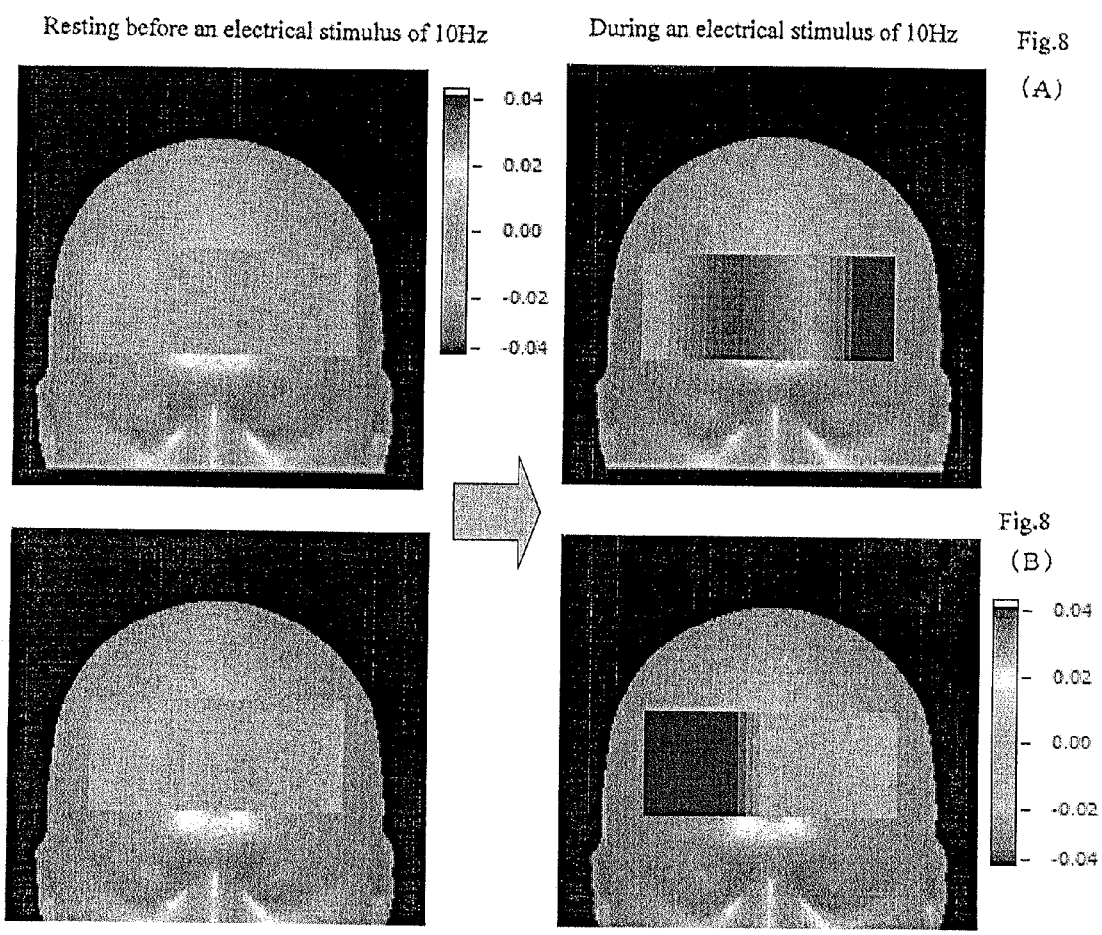
FIG. 8 (A) visually illustrates a change of the changed amount of total hemoglobin in the frontal lobe on resting before an electrical stimulus of 10 Hz is applied to a region adjacent to the center of the side of the hand palm between the first and second joints of the left hand thumb and on stimulation after such an electrical stimulus has been applied to the same region.

FIG. 8 (A) visually illustrates a change of the changed amount of total hemoglobin in the frontal lobe on resting before an electrical stimulus of 10 Hz is applied to a region adjacent to the center of the side of the hand palm between the first and second joints of the left hand thumb and on stimulation after such an electrical stimulus has been applied to the same region.

FIG. 8 (B) visually illustrates a change in the changed amount of oxygen saturation.

As can be seen from FIGS. 7 and 8, it was observed that the changed amount of total hemoglobin and the changed amount of oxygen saturation were dynamically decreased by the electrical stimulation of 10 Hz over a widened range.

When the electrical signals of 3 Hz and 10 Hz are applied to the targeted region of the left hand thumb in such a manner, respectively, the oxygen metabolism in the frontal lobe was opposite.

With the stimulation of 10 Hz, the oxygenation is reduced.

With the stimulation of 3 Hz, the total hemoglobin and oxygen saturation were increased.

The state of the frontal lobe was sensitively changed depending on the frequency of the electrical stimulation.

This suggests that the cognitive function is affected by the electrical stimulation.

Next, experiments when an acupunctural stimulation was performed as reference to compare it with the present invention will be described.

Figure 9:
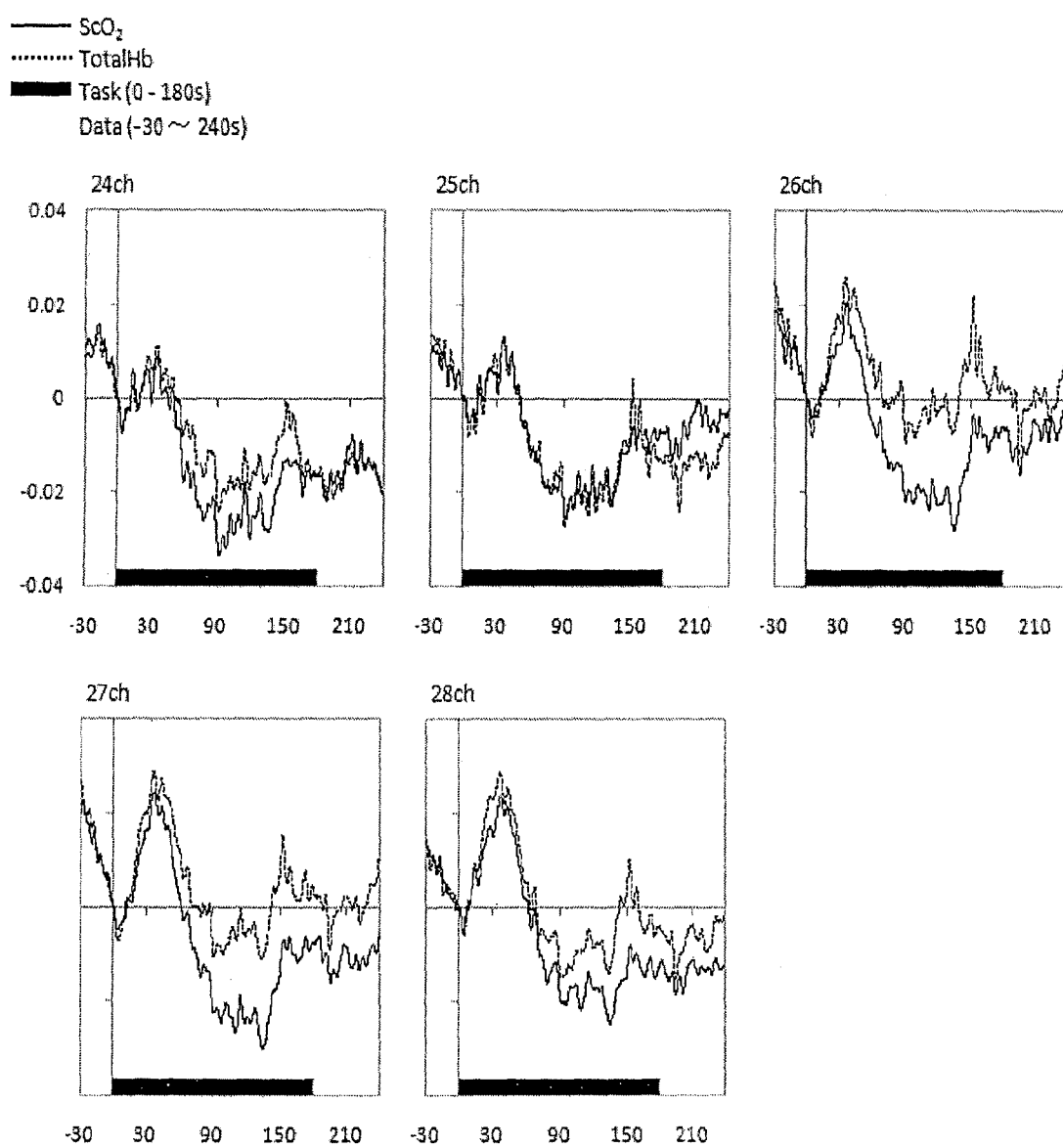
FIG. 9 shows graphs showing changes in the changed amount of total hemoglobin and the changed amount of oxygen saturation in the frontal lobe when an acupuncture stimulus is applied to a region adjacent to the center of the side of the hand palm between the first and second joints of the left hand thumb.

FIG. 9 shows graphs showing changes in the changed amount of total hemoglobin and the changed amount of oxygen saturation in the frontal lobe when an acupuncture stimulus is applied to a region adjacent to the center of the side of the hand palm between the first and second joints of the left hand thumb.

Here, the horizontal axis indicates time (s) while the vertical axis indicates the amount of change (mol/l). The time of stimulation is 180 seconds.

Figure 10:
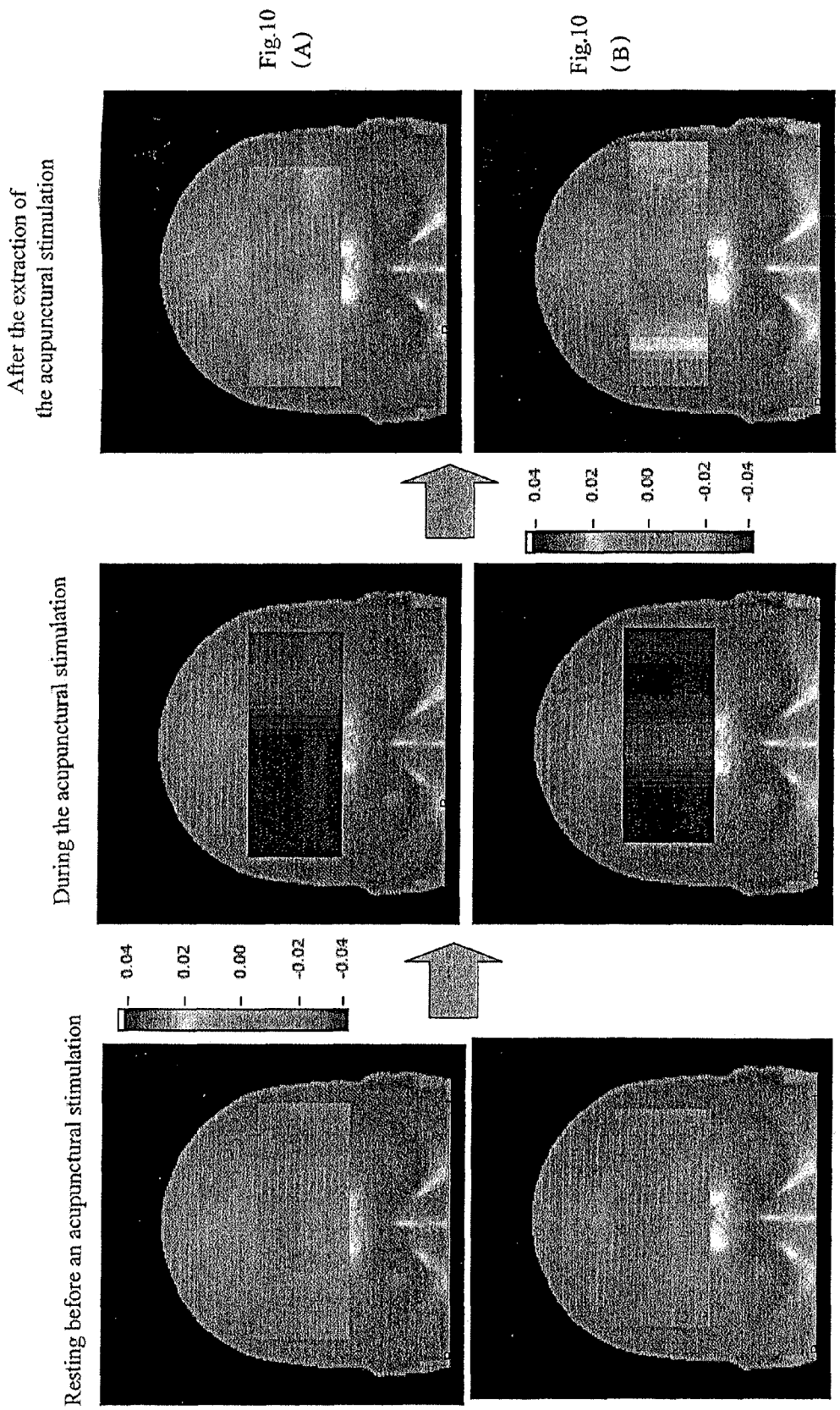
FIG. 10 (A) visually illustrates changes in the changed amount of total hemoglobin in the frontal lobe on resting when an acupuncture stimulus is applied to a region adjacent to the center of the side of the hand palm between the first and second joints of the left hand thumb, during the acupunctural stimulation and after the extraction of the acupunctural stimulation.

FIG. 10 (A) visually illustrates changes in the changed amount of total hemoglobin in the frontal lobe on resting when an acupunctural stimulation is applied to a region adjacent to the center of the side of the hand palm between the first and second joints of the left hand thumb, during the acupunctural stimulation and after the extraction of the acupunctural stimulation.

FIG. 10 (B) visually illustrates a change in the changed amount of oxygen saturation.

As can be seen from FIGS. 9 and 10, the acupunctural stimulation increased both the changed amount of total hemoglobin and the changed amount of oxygen saturation for 30-45 seconds on start of the acupuncture rotation.

However, the changed amount of total hemoglobin and changed amount of oxygen saturation were thereafter decreased continuously.

It is conceivable that this is the main effect of the acupuncture.

Further, the repeatability was recognized with respect to that the stimulation of 10 Hz is more similar to the acupunctural stimulation than the stimulation of 3 Hz.

Figure 11:
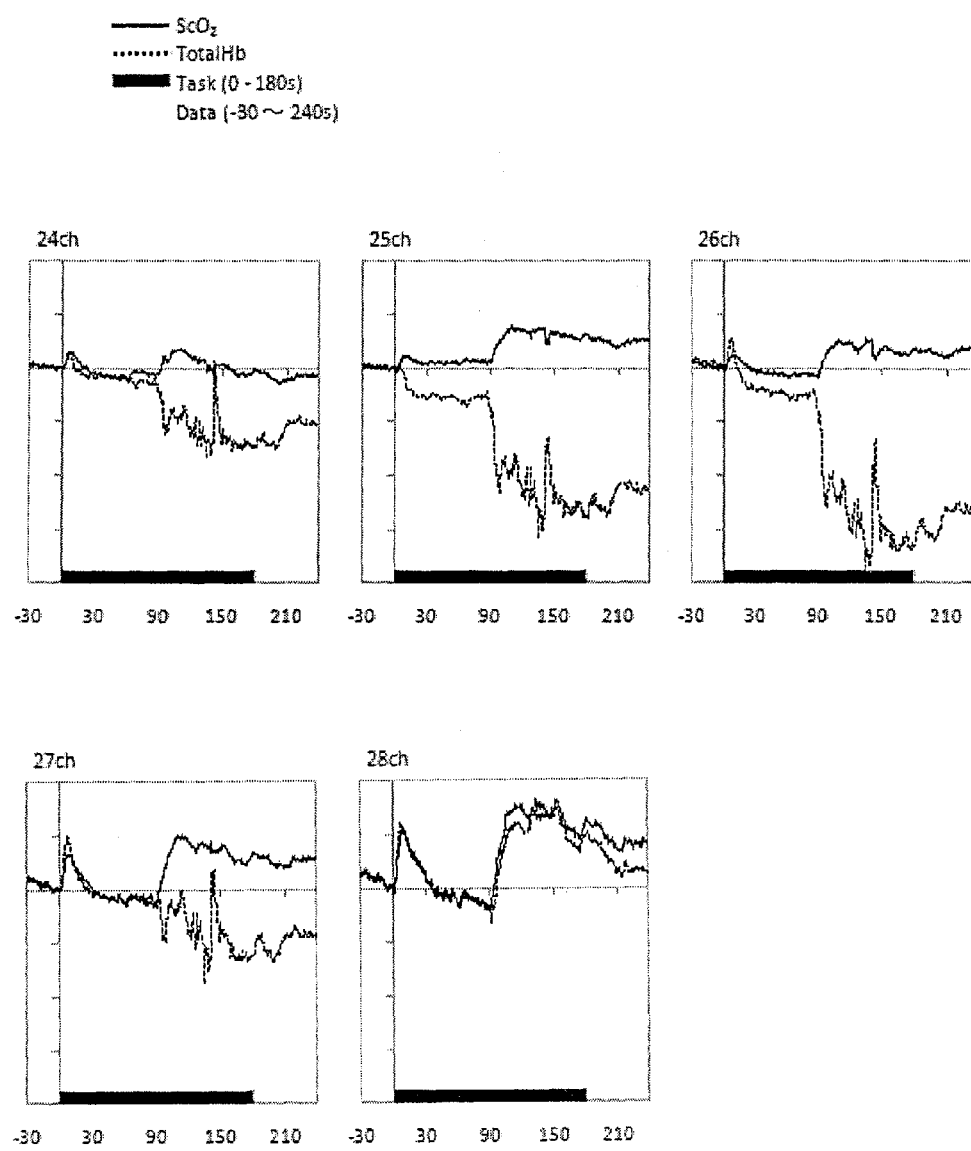
FIG. 11 shows graphs illustrating changes in the changed amount of total hemoglobin and the changed amount of oxygen saturation in the frontal lobe when an acupuncture stimulus is applied to a region adjacent to the tip of the outer from the first joint of the fourth right hand finger.

FIG. 11 shows graphs illustrating changes in the changed amount of total hemoglobin and the changed amount of oxygen saturation in the frontal lobe when an acupuncture stimulus is applied to a region adjacent to the tip of the outer from the first joint of the fourth right hand finger.

Here, the horizontal axis indicates time (s) while the vertical axis indicates the amount of change (mol/l). The time of stimulation is 180 seconds.

Figure 12:
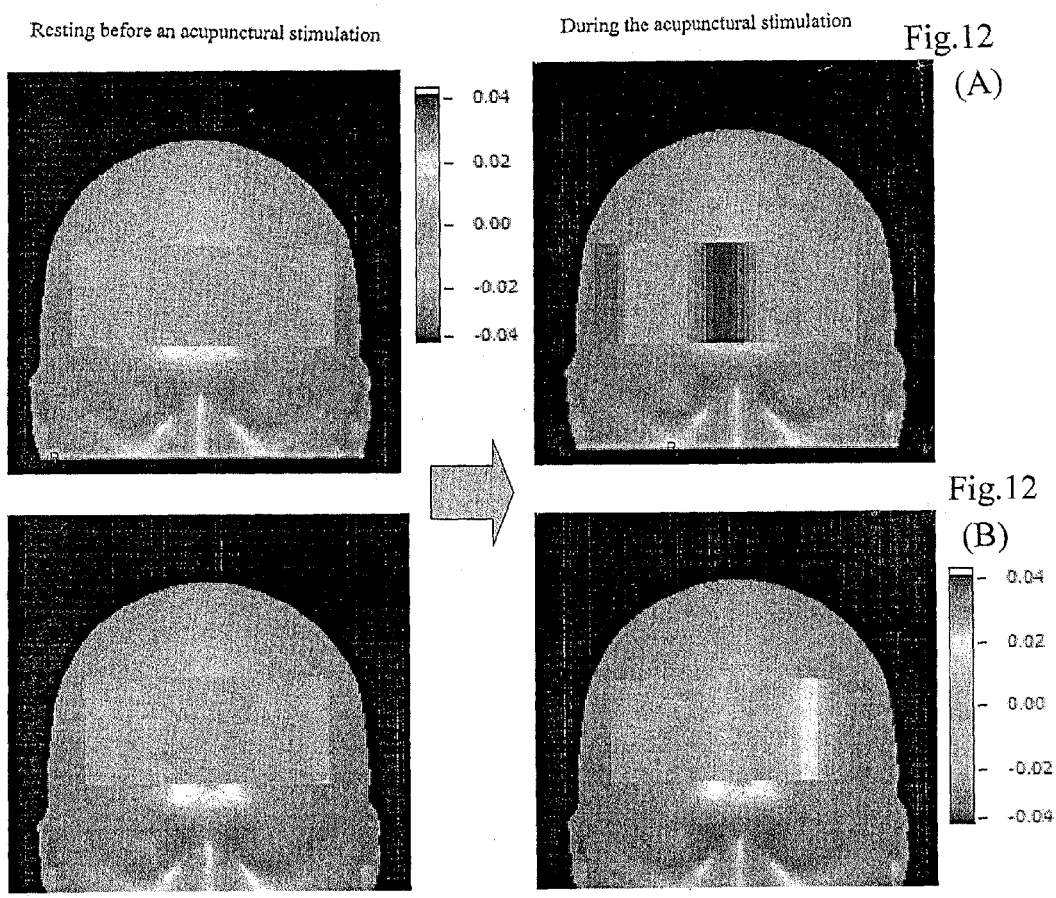
FIG. 12 (A) visually illustrates a change in the changed amount of total hemoglobin in the frontal lobe on resting before an acupuncture stimulus is applied to a region adjacent to the tip of the outer from the first joint of the fourth right hand finger and during the acupuncture.

FIG. 12 (A) visually illustrates a change in the changed amount of total hemoglobin in the frontal lobe on resting before an acupuncture stimulus is applied to a region adjacent to the tip of the outer from the first joint of the fourth right hand finger and during the acupunctural stimulation.

FIG. 12 (B) visually illustrates a change in the changed amount of oxygen saturation.

As can be seen from FIGS. 11 and 12, the increase of oxygen saturation and the decrease of total hemoglobin were observed in a part of the frontal lobe as a pain is being increased by the rotational acupunctural stimulations.

However, this was clearly different from the brain reaction due to the stimulation to the left hand thumb.

Figure 13:
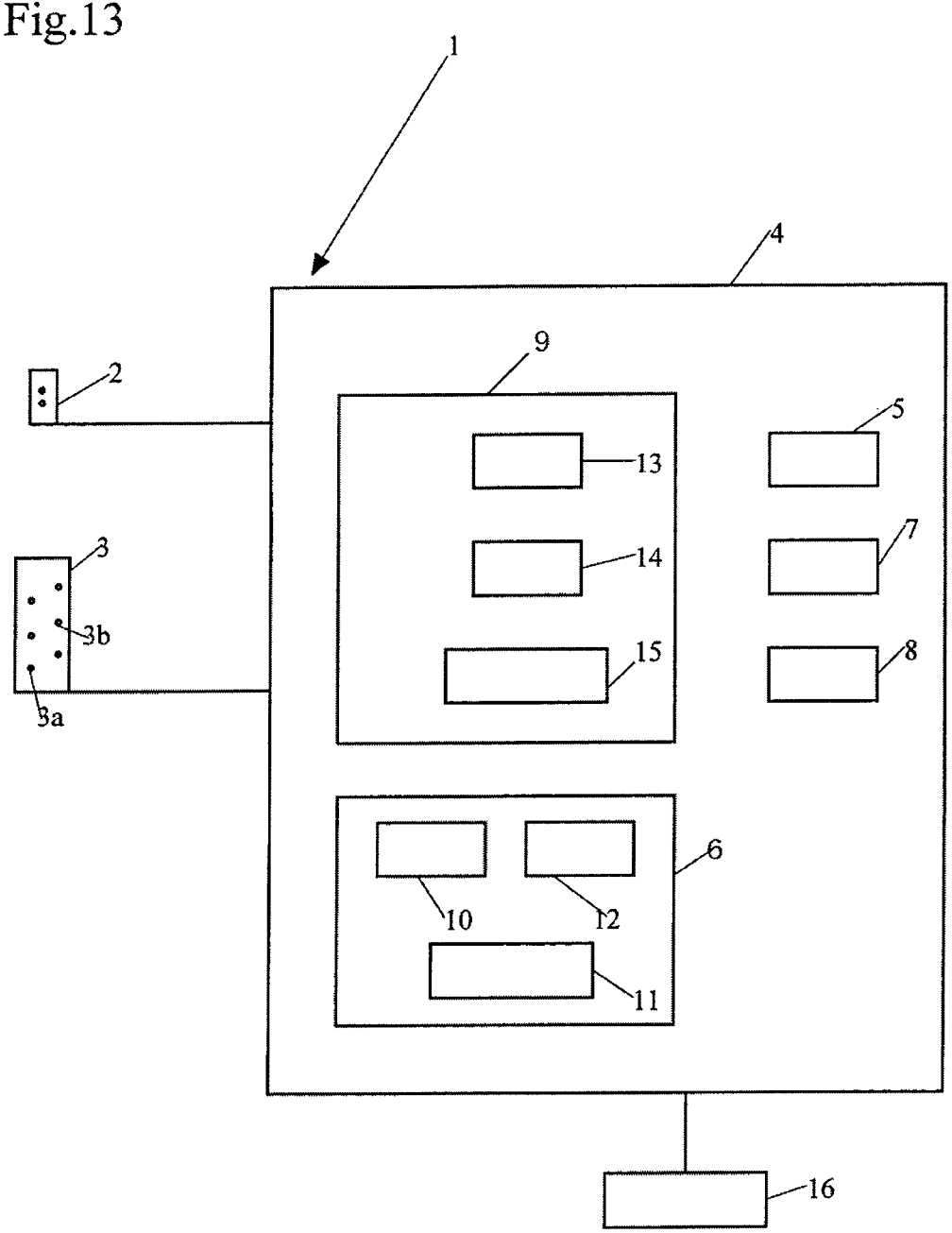
FIG. 13 is a block diagram illustrating a program according to one embodiment of the present invention.

FIG. 13 is a block diagram showing a program according to one embodiment of the present invention.

As shown in FIG. 13, the program 16 according to the embodiment of the present invention is configured to control the main apparatus body 4 of the brain state support apparatus 1 according to the embodiment of the present invention and to cause a computer to perform the process in the main apparatus body 4.

This program 16 may be recorded in a recording media such as magnetic disk, CD-ROM, semiconductor memory and may be downloaded through a communication network.

The present invention is not limited to the above mentioned embodiments, but can be modified to various other forms without departing from the range of technical features described in the subsequent claims.

For example, the main apparatus body 4 may be in the form of a personal computer or information terminal equipment.

[Industrial Applicability]

The brain state support apparatus 1 and program 16 according to the present invention can be used to support the brain state such that the brain state can be maintained in a relaxation or concentration mode or shifted to the other state, using the near-infrared spectroscopy (NIRS).

EXPLANATION OF REFERENCE NUMERALS

1: Brain State Support Apparatus
2: Stimulus Applying Device
2a: Stimulating Section
2b: Band Portion
2c: Loop Fasteners
3: Light detecting device
3a: Light Emitting Portions
3b: Light Receiving Portions
4: Main Apparatus Body
5: Input Section
6: Output Section
7: Communication Section
8: Storage Section
9: Control Section
10: Display Section
11: Speaker
12: Printing Section
13: Calculating Section
14: Determining Section
15: Stimulus Adjusting Section
16: Program

The invention claimed is:
1. A brain state support apparatus comprising:
an electrical stimulator configured for stimulating an acupoint in the human body in a region adjacent to the center of the side of the palm of the left hand between the first and second joints of the thumb, and including a first electrical stimulating portion adapted to stimulate the acupoint with an electrical signal of a first frequency of 3 Hz and a second electrical stimulating portion adapted to stimulate the acupoint with an electrical signal of a second frequency of 10 Hz, in order to change the amount of the total hemoglobin and the amount of oxygen saturation in the human body, and a retainer portion adapted to releasably hold the first and second electrical stimulating portion in engagement with the acupoint;
a light detector configured for detecting light information, the light detector having a light emitting section for irradiating the human body with a light at a predetermined region, and a light receiving section for receiving and sensing a light emitted from the light emitting section at the predetermined region and passing through the interior of the human body; and
a processor configured for controlling the electrical stimulator and the light detector, said processor including:
a calculator configured for calculating a changed amount of total hemoglobin that is the sum of a changed amount of oxyhemoglobin plus a changed amount of deoxyhemoglobin and a changed amount of oxygen saturation that is a difference between the changed amount of the oxyhemoglobin and the changed amount of the deoxyhemoglobin, based on light information detected by the light detector;
a determinator configured for determining whether the brain state of the human body is in at least one of a relaxation mode, a concentration mode and an intermediate mode, based on the changed amount of the total hemoglobin and the changed amount of oxygen saturation change which are calculated by the calculator during application of an electrical signal of the first frequency to the acupoint in the human body with the electrical stimulator; and
a stimulus adjustor configured for adjusting the electrical stimulator to stimulate the acupoint of the human body with the electrical signal of the first frequency at a predetermined interval of time when the brain state is to be maintained in or shifted to the relaxation mode, and to stimulate the acupoint of the human body with the electrical signal of the second frequency at a predetermined interval of time when the brain state is to be maintained in or shifted to the concentration mode; and
wherein when the electrical signal of the first frequency is applied to the acupoint, the oxygen metabolism in the frontal lobe increases relative to the oxygen metabolism in the frontal lobe in the absence of an electrical signal, and when the electrical signal of the second frequency is applied to the acupoint, the oxygen metabolism in the frontal lobe decreases relative to the oxygen metabolism in the frontal lobe in the absence of an electrical signal, with the oxygen saturation being reduced relative to the oxygen saturation in the absence of an electrical signal with the electrical stimulator adjusted to stimulate the acupoint with the electrical signal of the second frequency, and the total hemoglobin and the oxygen saturation being increased relative to the total hemoglobin and the oxygen saturation in the absence of an electrical signal with the electrical stimulator adjusted to stimulate the acupoint with the electrical signal of the first frequency.

2. The brain state support apparatus as claimed in claim 1, wherein the acupoint of the human body stimulated by the electrical stimulator is in the region of left thumb.

3. The brain state support apparatus as claimed in claim 1, wherein the region detected by the light detector is the cerebral frontal lobe.

4. The brain state support apparatus as claimed in claim 1, wherein the determinator is configured to determine that the brain state is in the relaxation mode when the changed amount of total hemoglobin is increased and also the changed amount of oxygen saturation is increased by stimulating the acupoint of the human body with an electrical signal of a first frequency; to determine that the brain state is in the concentration mode when the changed amount of total hemoglobin is decreased and also the changed amount of oxygen saturation is decreased by stimulating the acupoint of the human body with an electrical signal of a second frequency; and to determine that the brain state is in the intermediate mode in the other cases.

5. The brain state support apparatus as claimed in claim 1, wherein the stimulus adjustor is be configured to increase the quantity of stimulus when the brain state is to be shifted to the other modes rather than when the brain state is to be maintained at the same mode.

6. A method for changing oxygen metabolism and oxygen saturation in the brain, using the brain state support apparatus as claimed in claim 1, comprising the steps of:

applying the electrical stimulator to the acupoint;

adjusting the first electrical stimulating portion using the stimulus adjustor to apply the electrical signal of the first frequency of 3 Hz to increase the oxygen metabolism, the total hemoglobin, and the oxygen saturation in the frontal lobe relative to the oxygen metabolism, the total hemoglobin, and the oxygen saturation therein in the absence of an electrical signal, and adjusting the second electrical stimulating portion using the stimulus adjustor to apply the electrical signal of the second frequency of 10 Hz to decrease the oxygen metabolism and the oxygen saturation in the frontal lobe relative to the oxygen metabolism and the oxygen saturation in the frontal lobe in the absence of an electrical signal.

* * * * *